US00PP15551P2

(12) United States Plant Patent
Bevelander

(10) Patent No.: US PP15,551 P2
(45) Date of Patent: Feb. 8, 2005

(54) ***HIBISCUS* PLANT NAMED 'DENVER'**

(50) Latin Name: *Hibiscus rosa-sinensis*
Varietal Denomination: Denver

(75) Inventor: Marinus Jacobus Bevelander, Amstelveen (NL)

(73) Assignee: Coöperatieve Vereniging Werkgroep Hibiscus U.A., Rijsenhour (NL)

( * ) Notice: Subject to any disclaimer, the term of this patent is extended or adjusted under 35 U.S.C. 154(b) by 21 days.

(21) Appl. No.: 10/600,825

(22) Filed: Jun. 20, 2003

(51) Int. Cl.[7] ..... A01H 5/00
(52) U.S. Cl. ..... Plt./257
(58) Field of Search ..... Plt./257

*Primary Examiner*—Anne Marie Grunberg
*Assistant Examiner*—Annette H Para
(74) *Attorney, Agent, or Firm*—C. A. Whealy

(57) ABSTRACT

A new and distinct *Hibiscus* plant named 'Denver', characterized by its compact, upright and uniform plant habit that is appropriate for container production; freely branching habit; glossy medium green-colored leaves; freely and continuous flowering habit; orange and red bi-colored flowers; and good resistance to flower bud abscission.

1 Drawing Sheet

Botanical classification/cultivar designation: *Hibiscus rosa-sinensis* cultivar Denver.

BACKGROUND OF THE INVENTION

The present invention relates to a new and distinct cultivar of *Hibiscus*, botanically known as *Hibiscus rosa-sinensis,* and hereinafter referred to by the name 'Denver'.

The new *Hibiscus* is a product of a planned breeding program conducted by the Inventor in Amstelveen, The Netherlands. The objective of the breeding program is to create new compact freely-branching and freely-flowering *Hibiscus* cultivars appropriate for container production.

The new *Hibiscus* originated from a cross-pollination made by the Inventor in Amstelveen, The Netherlands in 1999, of a proprietary *Hibiscus rosa-sinensis* selection, identified as code number 239.2317, not patented, as the female, or seed, parent with a proprietary *Hibiscus rosa-sinensis* selection, designated as code number 5.17.14816, not patented, as the male, or pollen, parent. The cultivar Denver was discovered and selected by the Inventor as a flowering plant within the progeny of the stated cross-pollination in a controlled environment in Amstelveen, The Netherlands, in 2000.

Asexual reproduction of the new *Hibiscus* by vegetative terminal cuttings in a controlled environment in Amstelveen, The Netherlands since 2000, has shown that the unique features of this new *Hibiscus* are stable and reproduced true to type in successive generations.

SUMMARY OF THE INVENTION

The cultivar Denver has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Denver'. These characteristics in combination distinguish 'Denver' as a new and distinct cultivar:

1. Compact, upright and uniform plant habit that is appropriate for container production.
2. Freely branching habit.
3. Glossy medium green-colored leaves.
4. Freely and continuous flowering habit.
5. Orange and red bi-colored flowers.
6. Good resistance to flower bud abscission.

Compared to plants of the parents, the proprietary *Hibiscus* selections, plants of the new *Hibiscus* are more upright, more freely branching, and more freely flowering.

Plants of the new *Hibiscus* are similar to plants of the *Hibiscus* cultivar Hanne, not patented. However, in side-by-side comparisons conducted in Amstelveen, The Netherlands, plants of the new *Hibiscus* differed from plants of the cultivar Hanne in the following characteristics:

1. Plants of the new *Hibiscus* were shorter than plants of the cultivar Hanne.
2. Plants of the new *Hibiscus* were more upright and more rounded than plants of the cultivar Hanne.
3. Leaves of plants of the new *Hibiscus* were longer and narrower than leaves of plants of the cultivar Hanne.
4. Plants of the new *Hibiscus* had larger flowers than plants of the cultivar Hanne.
5. Plants of the new *Hibiscus* were more freely flowering than plants of the cultivar Hanne.
6. Flowers of plants of the new *Hibiscus* were more red in color than flowers of plants of the cultivar Hanne.
7. Flower peduncles of plants of the new *Hibiscus* were longer and thicker than flower peduncles of plants of the cultivar Hanne.

BRIEF DESCRIPTION OF THE PHOTOGRAPH

The accompanying colored photograph illustrates the overall appearance of the new *Hibiscus*, showing the colors as true as it is reasonably possible to obtain in colored reproductions of this type. Colors in the photograph may differ slightly from the color values cited in the detailed botanical description which accurately describe the colors of the new *Hibiscus*.

The photograph comprises a side perspective view of a typical flowering plant of 'Denver' grown in a container.

DETAILED BOTANICAL DESCRIPTION

The aforementioned photograph and following observations and measurements describe plants grown in Amstelveen, The Netherlands, grown in 15-cm container in a glass-covered greenhouse during the spring and summer under conditions which closely approximate commercial production. During the production of the plants, day and night temperatures ranged from 15 to 25° C. and light levels were about 500 kilolux. Plants were about two years old when the photograph and the description were taken. In the description, color references are made to The Royal Horticultural Society Colour Chart, 1986 Edition, except where general terms of ordinary dictionary significance are used.

Botanical classification: *Hibiscus rosa-sinensis* cultivar Denver.

Parentage:

*Female or seed parent.*—Proprietary selection of *Hibiscus rosa-sinensis* designated as code number 239.2317, not patented.

*Male or pollen parent.*—Proprietary selection of *Hibiscus rosa-sinensis* designated as code number 5.17.14816, not patented.

Propagation:

*Type.*—By vegetative terminal cuttings.

*Time to initiate roots.*—About 25 days at a temperature of 23° C.

*Time to produce a rooted young plant.*—About 40 days at a temperature of 22° C.

*Root description.*—Thick; whitish in color.

*Rooting habit.*—Moderately vigorous; freely branching.

Plant description:

*Plant form and growth habit.*—Compact, upright and uniform plant habit; appropriate for container production. Vigorous growth habit.

*Branching habit.*—Freely branching, usually about three or four lateral branches.

*Plant height.*—About 20 to 25 cm.

*Plant diameter* (*area of spread*).—About 35 to 40 cm.

*Lateral branch description.*—Length: About 10 cm. Diameter: About 8 mm. Internode length: About 2 to 2.5 cm. Texture: Smooth, glabrous. Color: Close to 146A overlain with close to 187A.

*Foliage description.*—Arrangement: Alternate, simple. Length: About 7 to 8 cm. Width: About 4 to 5 cm. Shape: Cordate. Apex: Acute. Base: Cordate. Margin: Serrate. Texture, upper surface: Glabrous; leathery. Texture, lower surface: Slightly pubescent. Venation pattern: Pinnate. Color: Developing leaves, upper surface: 146A; glossy. Developing leaves, lower surface: 146A. Fully expanded leaves, upper surface: Darker than 146A; glossy. Fully expanded leaves, lower surface: 146A. Venation, upper surface: 146A. Venation, lower surface: Lighter than 146A. Petiole: Length: About 3 cm. Diameter: About 3 mm. Texture, upper and lower surfaces: Smooth, glabrous. Color, upper and lower surfaces: Darker than 146A.

Flower description:

*Flower arrangement/appearance.*—Rounded flowers arranged singly at terminal leaf axils. Freely and continuous flowering with usually about five to six flower buds and/or open flowers per terminal apex. Flowers face upright and outwardly. Flowers are open for about one day. Flowers persistent. Flowers not fragrant.

*Natural flowering season.*—Usually spring and summer or during periods of warm weather.

*Flower diameter.*—About 10 cm.

*Flower length* (*height*).—About 3 to 4 cm.

*Flower bud* (*just before showing color*).—Resistance to abscission: Plants of the new *Hibiscus* have been observed to resist flower bud drop. Length: About 4 to 5 cm. Diameter: About 1 to 1.5 cm. Shape: Elliptical. Color: 146A.

*Petals.*—Arrangement: Corolla consists of five petals that are overlapping towards apex. Length: About 6 to 7 cm. Width: About 5 to 6 cm. Shape: Spatulate or fan-shaped. Apex: Rounded. Base: Attenuate. Margin: Entire. Texture, upper and lower surfaces: Smooth, glabrous, satiny. Color: When opening and fully opened, upper surface: Towards the margins, 23B; towards the base, 45D. When opening and fully opened, lower surface: 24B. Throat: Close to 45A.

*Sepals.*—Appearance: Five or six sepals fused into a companulate-shaped calyx. Length: About 2 cm. Width: About 1 cm. Shape: Narrowly oblong. Apex: Acute. Base: Fused. Margin: Cleft. Texture, upper and lower surfaces: Smooth. Color, upper and lower surfaces: Close to 146A.

*Peduncles.*—Length: About 7 mm. Diameter: About 3 mm. Angle: Slightly bent. Strength: Strong, rigid. Texture: Smooth. Color: Darker than 146A.

*Reproductive organs.*—Androecium: Stamen number: Numerous, about 60 per flower. Anther shape: Globular. Anther length: About 1 mm. Anther color: 12A. Amount of pollen: Abundant. Pollen color: 15A. Gynoecium: Pistil number: One per flower. Pistil length: About 6 to 7 cm. Style length: About 4 to 5 cm. Style texture: Smooth, waxy. Style color: 45D. Stigma appearance: Five, rounded. Stigma color: 17A. Ovary color: Reddish white.

*Fruit/seed.*—Fruit and seed production has not been observed.

Disease/pest resistance: Plants of the new *Hibiscus* have not been observed to be resistant to pathogens and pests common to *Hibiscus*.

It is claimed:

1. A new and distinct *Hibiscus* plant named 'Denver', as illustrated and described.

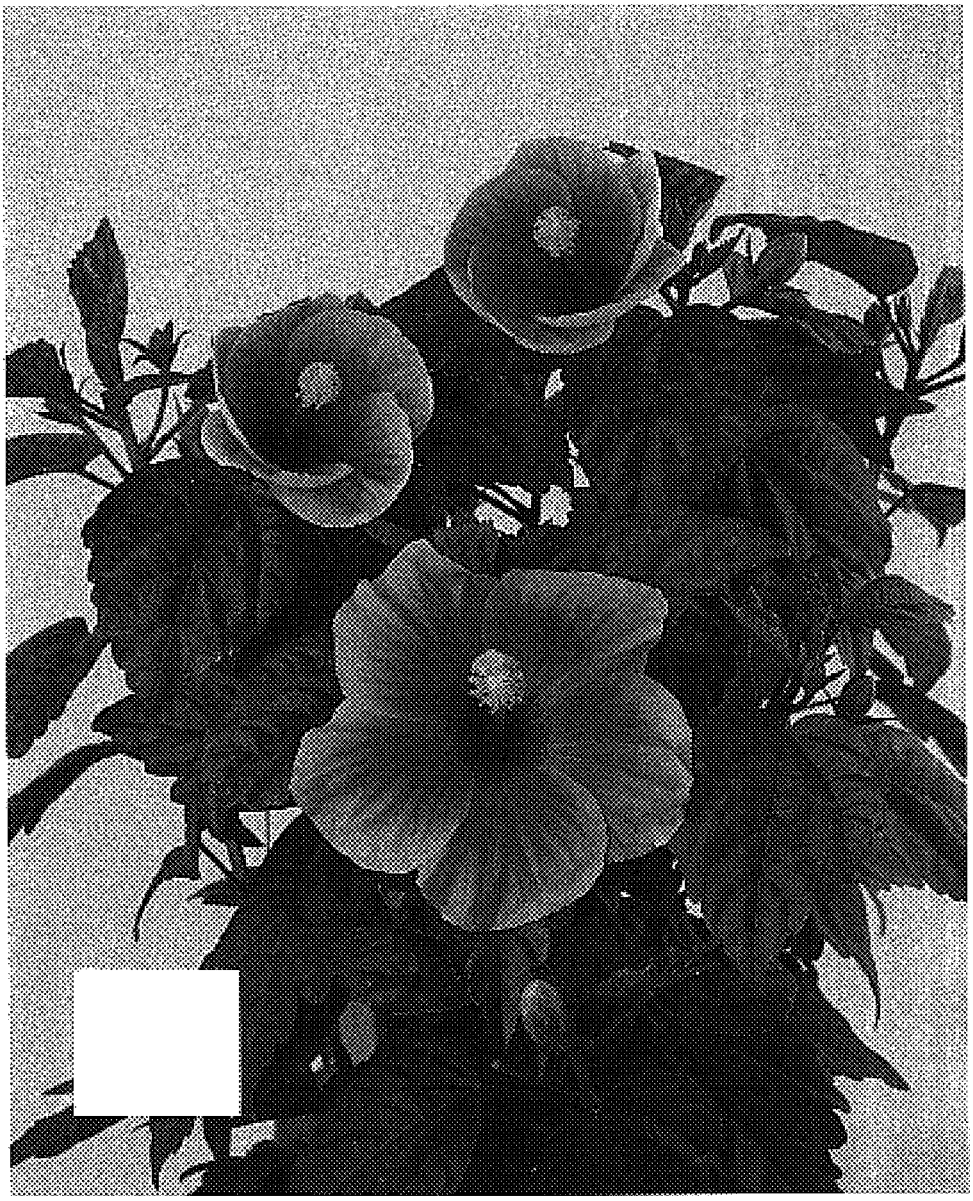

* * * * *